US011419520B2

(12) United States Patent
Olivo et al.

(10) Patent No.: US 11,419,520 B2
(45) Date of Patent: Aug. 23, 2022

(54) METHOD AND SYSTEM FOR RESPIRATORY MEASUREMENT

(71) Applicant: Agency for Science, Technology and Research, Singapore (SG)

(72) Inventors: Malini Olivo, Singapore (SG); Gurpreet Singh, Singapore (SG); Renzhe Bi, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 176 days.

(21) Appl. No.: 16/612,722

(22) PCT Filed: May 15, 2018

(86) PCT No.: PCT/SG2018/050238
§ 371 (c)(1),
(2) Date: Nov. 11, 2019

(87) PCT Pub. No.: WO2018/212715
PCT Pub. Date: Nov. 22, 2018

(65) Prior Publication Data
US 2020/0163591 A1    May 28, 2020

(30) Foreign Application Priority Data

May 15, 2017 (SG) .......................... 10201703974R

(51) Int. Cl.
*A61B 5/08* (2006.01)
*A61B 5/113* (2006.01)
*A61B 5/00* (2006.01)

(52) U.S. Cl.
CPC ............ *A61B 5/0816* (2013.01); *A61B 5/113* (2013.01); *A61B 5/6822* (2013.01);
(Continued)

(58) Field of Classification Search
CPC ..... A61B 5/113; A61B 5/6822; A61B 5/6823; A61B 5/6833; A61B 5/7257; A61B 5/7278; A61B 5/0816; A61B 5/0823
See application file for complete search history.

(56) References Cited

U.S. PATENT DOCUMENTS 4,308,872 A   1/1982  Watson et al.
6,081,742 A * 6/2000  Amano ............... A61B 5/0205
                                                      600/484

(Continued)

FOREIGN PATENT DOCUMENTS

JP   2002204800 A   7/2002
JP   2005253590 A   9/2005
(Continued)

OTHER PUBLICATIONS

Nilsson et al., "Respiration can be Monitored by Photoplethysmography with High Sensitivity and Specificity Regardless of Anaesthesia and Ventilatory Mode," ACTA Anaesthesiologica Scandinavica, vol. 49, No. 8, Sep. 1, 2005, pp. 1157-1162.
(Continued)

*Primary Examiner* — Daniel L Cerioni
*Assistant Examiner* — Raymond P Dulman
(74) *Attorney, Agent, or Firm* — Shackelford, Bowen, McKinley & Norton, LLP

(57) ABSTRACT

Method for measuring respiratory vibration on a human or animal skin, including emitting an emission light at a first position on the skin and receiving a diffused light from the emission light at a second position on the skin; storing a vibration signal including a light intensity of the diffused light received over time; wherein the vibration signal corresponds to a mechanical vibration of the skin, and extracting a respiratory parameter from the vibration signal. In particular, at least one of the first position and the second position is in proximity to or at a trachea, a neck or a chest.

(Continued)

The system for carrying out the method includes an emitter, a receiver, a circuit, and a processing unit. A set of a sensor module and a skin adhesive patch is also provided.

20 Claims, 9 Drawing Sheets

(52) U.S. Cl.
CPC .......... *A61B 5/6823* (2013.01); *A61B 5/6833* (2013.01); *A61B 5/7257* (2013.01); *A61B 5/7278* (2013.01); *A61B 5/0823* (2013.01)

(56) References Cited

U.S. PATENT DOCUMENTS

| | | | |
|---|---|---|---|
| 6,498,652 B1 | 12/2002 | Varshneya et al. | |
| 6,702,752 B2 | 3/2004 | Dekker | |
| 7,641,618 B2 | 1/2010 | Noda et al. | |
| 7,720,534 B2 | 5/2010 | Bardy et al. | |
| 7,740,588 B1 | 6/2010 | Sciarra | |
| 8,506,480 B2 | 8/2013 | Banet et al. | |
| 8,641,631 B2 | 2/2014 | Sierra et al. | |
| 8,740,807 B2 | 6/2014 | Banet et al. | |
| 2003/0073919 A1 | 4/2003 | Hampton et al. | |
| 2005/0215915 A1 | 9/2005 | Noda et al. | |
| 2006/0217612 A1* | 9/2006 | Ouchi | A61B 5/0507 600/407 |
| 2007/0282227 A1* | 12/2007 | Nanba | A61B 5/0059 600/595 |
| 2008/0082018 A1* | 4/2008 | Sackner | A61B 5/113 600/538 |
| 2011/0066039 A1 | 3/2011 | Banet et al. | |
| 2011/0125044 A1* | 5/2011 | Rhee | A61B 5/113 600/534 |
| 2012/0197093 A1* | 8/2012 | LeBoeuf | A61B 5/026 600/301 |
| 2013/0060098 A1* | 3/2013 | Thomsen | A61B 5/14551 600/301 |
| 2014/0155729 A1* | 6/2014 | Saitoh | A61B 5/1128 600/407 |
| 2014/0180154 A1 | 6/2014 | Sierra et al. | |
| 2014/0221852 A1 | 8/2014 | Van Slyke et al. | |
| 2014/0236037 A1 | 8/2014 | Banet et al. | |
| 2014/0275854 A1 | 9/2014 | Venkatraman et al. | |
| 2015/0148625 A1 | 5/2015 | Benaron | |
| 2016/0345862 A1 | 12/2016 | Li | |
| 2017/0251930 A1* | 9/2017 | Machida | A61B 5/681 |
| 2018/0296092 A1* | 10/2018 | Hassan | G10L 25/66 |

FOREIGN PATENT DOCUMENTS

| | | |
|---|---|---|
| JP | 2008173280 A | 7/2008 |
| JP | 2016501582 A | 1/2016 |
| JP | 2017506920 A | 3/2017 |
| JP | 2017510390 A | 4/2017 |
| WO | 0119433 A1 | 3/2001 |
| WO | 2006117780 A2 | 11/2006 |
| WO | 2012103273 A2 | 8/2012 |
| WO | 2014135976 A2 | 9/2014 |
| WO | 2016174303 A1 | 11/2016 |

OTHER PUBLICATIONS

Extended European Search Report for European Patent Application No. 18803085.2 dated Mar. 22, 2021, pp. 1-8.
Zhang et al., "Development of a Respiratory Inductive Plethysmography Module Supporting Multiple Sensors for Wearable Systems," Sensors, vol. 12, 2012, pp. 13167-13184.
Gupta, Amit K., "Respiration Rate Measurement Based on Impedance Pneumography," Texas Instruments Application Report., Feb. 2011, pp. 1-10.
Karlen et al., "Respiratory Rate Estimation Using Respiratory Sinus Arrhythmia from Photoplethysmography," IEEE Eng. Med Biol. Soc., 2011, pp. 1201-1204.
Kim et al., "Reflectance Spectrometry of Normal and Bruised Human Skins: Experiments and Modeling," Physiological Measurement, vol. 33, 2012, pp. 159-175.
International Search Report for International Application No. PCT/SG2018/050238 dated Aug. 27, 2018, pp. 1-4.
Written Opinion of the International Searching Authority for International Application No. PCT/SG2018/050238 dated Aug. 27, 2018, pp. 1-5.
International Preliminary Report on Patentability for International Application No. PCT/SG2018/050238 dated Jan. 30, 2019, pp. 1-13.
Office Action for Chinese Application No. 2018800314452 dated Dec. 6, 2021, pp. 1-14.
Office Action for Japanese Patent Application No. 2019-563189 dated Feb. 8, 2022, pp. 1-7.
Ackermann et al., "Designing the Optical Interface of a Transcutaneous Optical Telemetry Link," IEEE Transactions on Biomedical Engineering, vol. 55, No. 4, pp. 1365-1373, Apr. 2008.

* cited by examiner

A-A

METHOD AND SYSTEM FOR RESPIRATORY MEASUREMENT

CROSS-REFERENCE TO RELATED APPLICATION

This application claims the benefit of priority of Singapore patent application No. 10201703974R filed on May 15, 2017, the contents of it being hereby incorporated by reference in its entirety for all purposes.

TECHNICAL FIELD

Various aspects of this disclosure relate to a method for measuring respiratory vibration on a human or animal skin. Various aspects of this disclosure relate to a system for performing the method for measuring respiratory vibration on a human or animal skin. Various aspects of this disclosure relate to a set of a sensor module and a skin adhesive patch.

BACKGROUND

Healthcare facilities worldwide still measure respiration manually by counting and timing chest movements. In clinical departments that are fast-paced in nature and that have either high patient volumes or require more accurate measurements (e.g. emergency and respiratory wards), manual methods of counting respiration can be slow, laborious and highly subjective. While potential solutions such as electrocardiography (ECG) and capnography (CPG) have been explored for more objective monitoring of respiration, they are not fast enough due to long setup times to get patient and system ready and prolonged periods of connection to patients. Furthermore, such ECG/CPG based solutions can be costly, are generally sufficient for patients in high dependency units, and may be impractical to deploy in a remote setting. The known solutions that can be used to measure respiration in a clinical setting are those based on electrical, acoustic and measuring concentrations of carbon-dioxide (capnography). The main bottleneck of such techniques is that they are generally not accessible to patients at large, especially in large-volume clinical settings such as emergency departments, and they are cumbersome and not very efficient to use. They require long setup times and patient movements are restricted.

Thus, there is a need for providing a convenient and accurate method and an apparatus for respiratory measurement.

SUMMARY

Various embodiments may provide a method for measuring respiratory vibration on a human or animal skin. The method may include: emitting an emission light at a first position on the skin and receiving a diffused light from the emission light at a second position on the skin. The second position is at a distance apart from the first position. The method may include storing a vibration signal, which vibration signal may include a light intensity of the diffused light received over time. The vibration signal may correspond to a mechanical vibration of the skin. The method may include extracting a respiratory parameter from the vibration signal.

Various embodiments may provide a system for performing the method according to the present disclosure. The system may include an emitter and a receiver. The emitter may be configured to emit an emission light at the first position on skin. The receiver may be configured to receive a diffused light from the emission light at the second position on skin. The second position is at a distance apart from the first position. The system may include a circuit. The circuit may be configured to store a vibration signal corresponding to the light intensity of the diffused light received over a time. The system may include a processing unit. The processing unit may be configured to extract a respiratory parameter from the vibration signal.

Various embodiments may provide a set of a sensor module and a skin adhesive patch. The skin adhesive patch may include a first surface which may be placed on a skin and a second surface which may cooperate with the sensor module to fixate the sensor module to the patch. The sensor module may include an emitter and a receiver. The emitter may be configured to emit an emission light at the first position on the skin. The receiver may be configured to receive a diffused light from the emission light at the second position on the skin. The second position is at a distance apart from the first position. The sensor module may include a circuit. The circuit may be configured to store a vibration signal corresponding to a light intensity of the diffused light received over a time. The skin adhesive patch may include a window region, configured to allow optical coupling of the emitter to skin, and of the receiver to skin.

BRIEF DESCRIPTION OF THE DRAWINGS

The invention will be better understood with reference to the detailed description when considered in conjunction with the non-limiting examples and the accompanying drawings, in which.

DETAILED DESCRIPTION

Figure 1:
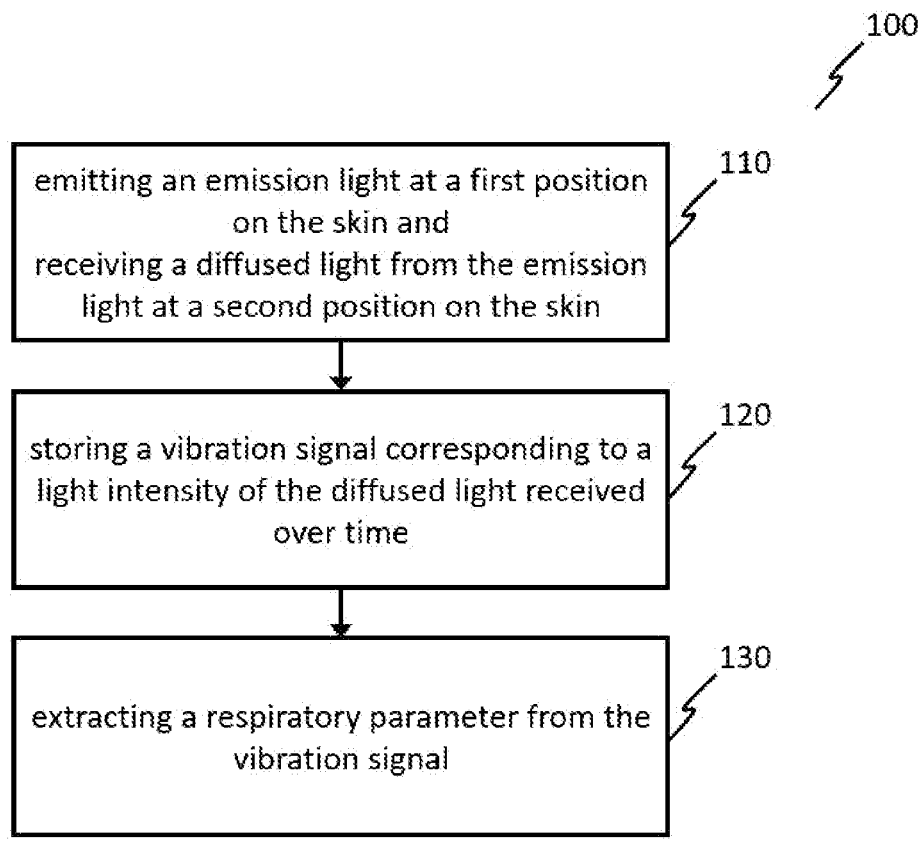
FIG. 1 shows a flowchart of the method 100 according to various embodiments.

The following detailed description refers to the accompanying drawings that show, by way of illustration, specific details and embodiments in which the invention may be practiced. These embodiments are described in sufficient detail to enable those skilled in the art to practice the invention. Other embodiments may be utilized and structural, and logical changes may be made without departing from the scope of the invention. The various embodiments are not necessarily mutually exclusive, as some embodiments can be combined with one or more other embodiments to form new embodiments.

Embodiments described in the context of a method may be analogously valid for the system and vice-versa. Similarly, embodiments described in the context of a system may be analogously valid for a set of a sensor module and a skin adhesive patch, and vice-versa. Also, embodiments described in the context of a method may be analogously valid for a set of a sensor module and a skin adhesive patch, and vice-versa.

Features that are described in the context of an embodiment may correspondingly be applicable to the same or similar features in the other embodiments. Features that are described in the context of an embodiment may correspondingly be applicable to the other embodiments, even if not explicitly described in these other embodiments. Furthermore, additions and/or combinations and/or alternatives as described for a feature in the context of an embodiment may correspondingly be applicable to the same or similar feature in the other embodiments.

In the context of various embodiments, the articles "a", "an" and "the" as used with regard to a feature or element include a reference to one or more of the features or elements.

As used herein, the term "and/or" includes any and all combinations of one or more of the associated listed items.

Various embodiments may provide a method for measuring respiratory vibration on a human or animal skin. According to various embodiments, the term "respiratory vibration" may mean a mechanical vibration caused on the skin, e.g. the skin subsurface, by the respiratory tract. One example of a cause for respiratory vibration is breathing.

According to various embodiments, the method may include: emitting an emission light at a first position on the skin and receiving a diffused light from the emission light at a second position on the skin. The second position is at a distance apart from the first position. The distance may be selected from 2 mm to 20 mm, for examples from 5 mm to 15 mm. Exemplary distances are 5 mm and 10 mm. The distance may be measured as the distance between the center of light emission of an emitter's end which end is to be positioned proximal to skin and the center of light detection of a receiver's end which end is to be positioned proximal to skin.

The method may include storing a vibration signal corresponding to a light intensity of the diffused light received over time.

According to various embodiments, the term "vibration signal" may mean a received signal in electronic form corresponding to a mechanical vibration of the skin, wherein the mechanical vibration of the skin may include the respiratory vibration signal. A plurality of light intensity values obtained over time may include, or may form, the vibration signal. For example, the light intensity may be received with a receiver, for example a photodiode, the electrical signal from the photodiode over time may be considered the vibration signal. In another example, the light intensity received by a receiver, for example by a photodetector or a photodiode, may be converted from analog to digital form and may further be stored in a memory. A plurality of light intensity values stored over time in digital form may form a vibration signal in digital form.

It was surprisingly found that the vibration signal is due to the mechanical vibrations, for example, in proximity to a trachea, along the neck area or around the chest area, which mechanical vibrations result from breathing. The vibration signal due to breathing, as obtained in various embodiments, is in fact much stronger as compared to other optical based methods such as the photo-plethysmogram (PPG). The PPG method is generally used in pulse oximeters and smart wrist-watches to measure the heart rate of a person, at an extremity of the person's body, and can be used to indirectly infer the respiratory rate. Although it is also possible to infer respiration with a pulse-oximeter, this method is indirect and is not accurate for clinical efforts. Accordingly pulse-oximeter devices are configured to be used at extremities of the body, where the respective PPG signals may be acquired. In contrast, the method of the present disclosure uses the fact that the membrane just below of the skin on the trachea area, is expanding and contracting when breathing. Due to expansion and contraction, the light absorption is changing, and hence, the diffuse reflected optical signal (the diffused light), carrying the vibration signal, is changing as well. The vibration signal carries a pattern corresponding to the breathing rate. In fact, it was found that the respiratory modulations may be observed from the raw analog signal measured at the receiver. The method according to various embodiments is more direct and can be more accurate compared to other optical based methods, since it does not necessarily require any form of additional signal processing techniques to observe the respiratory rate (note that respiration rate calculation from PPG is an indirect method). Furthermore, it can move away from measurements at body extremities, for example the arm, finger or other areas, which are typical areas for measuring PPG based respiratory rates—and some of these areas may be of concern especially with respect to user experiences. It is important to note that the vibration signal measured is not a PPG signal but rather a signal due to the mechanical vibration of the skin.

It was surprisingly found that the method and system as used herein may be used to obtain very accurate respiratory information, in a simple manner.

According to various embodiments, the method may include extracting a respiratory parameter from the vibration signal. According to various embodiments, the respiratory parameter may be: breath cycle count, frequency or rate, depth, inhalation-to-exhalation ratio (IER), durations of inhalation, retention, exhalation, hold, consistency, smoothness, transition. For example, the respiratory parameter may be breath frequency or breath cycle count. Accordingly, extracting the respiratory parameter may include determining at least one of: breath frequency, breath cycle count. The respiratory parameters may be respiratory parameters of periodic signal. For example the respiratory parameters: breath cycle count, frequency or rate, depth, inhalation-to-exhalation ratio (IER), durations of inhalation, retention, exhalation, and hold, consistency, smoothness, transition, may be respiratory parameters of periodic signal.

According to various embodiments, the method may further include applying a low-pass filter on the vibration signal. The low-pass filter may be applied on the vibration signal for determining a respiratory parameter, in particular for determining a respiratory parameter of periodic signal. The low-pass filter may be an electronic analog filter for filtering the vibration signal in analog form, e.g., before a conversion in digital form. Alternatively or in addition, the low-pass filter may a digital filter for filtering the vibration signal in digital form. For example, the low pass filter may have a cut-off frequency of 1 Hz, or 0.8 Hz. The cut-off frequency may be a half-power point of −3 dB. It was found that with the low pass filter a better signal to noise ratio may be obtained, in particular for determining a respiratory parameter.

According to various embodiments, the term "breath" as, e.g., in "breath cycle count", may refer to a cycle of air intake into the lungs and then expelling it.

According to various embodiments, the method may include generating a spectrum in the frequency domain from the vibration signal, which vibration signal is in the time domain. For example, an FFT transformation may be applied to the vibration signal for obtaining the spectrum. In one example, the breath frequency may be obtained from a frequency corresponding to a peak in the spectrum. For example, for human respiration, the breath frequency may be obtained between the frequencies of 0.15 Hz and 1 Hz, for example between 0.2 and 0.8 Hz. The breath rate may be directly calculated from the breath frequency.

Besides monitoring the respiration of a person, the proposed method can also be used to monitor a person's cough and/or speech. When a person coughs, spikes can be observed from the photodetector output. Similarly, when a person speaks, the breathing signal is modulated and can be observed from the photodetector output. By tracking such respiratory behaviors, it may be possible to use the proposed method to track 1) respiratory illnesses such as asthma and chronic obstructive pulmonary disease (COPD), 2) sleep disorders such as obstructive sleep apnea, 3) stress and wellbeing, 4) speech communication and 5) fitness performances.

According to various embodiments, the method according to various embodiments may include isolating signals with a frequency range between the frequencies of 0.15 Hz and 1 Hz, for example between 0.2 and 0.8 Hz.

According to various embodiments, the respiratory parameter may be a cough event or cough events count. Accordingly, extracting the respiratory parameter may include determining one or more cough events. For example, a cough event may be characterized by a higher amplitude, for example 2 times or higher, than the average breathing amplitude, and a duration period shorter, for example by half, by a third, or less, than the average breathing period. It was found that a cough event has a very strong signal. Consequently, a cough event may also be detected, from the vibration signal before the low-pass filter, if such filter is provided.

According to various embodiments, the respiratory parameter may be a speech event or information related to a speech event. Accordingly, extracting the respiratory parameter may include determining one or more speech events. The speech may be filtered from the vibration signal by a speech filter. The speech filter may be a band pass filter, for example with band pass between 100 Hz to 17 kHz. Thus speech may be easily distinguished from other respiratory parameters, in particular from respiratory parameters of periodic signal.

Various embodiments may provide a system for performing the method according to the present disclosure. The system may include an emitter and a receiver.

In the context of the present disclosure and also according to various embodiments, the term "system" may mean a system implemented as an apparatus. For example as an apparatus which may be worn by a user, for example at a user's neck area.

According to various embodiments, the emitter may be configured to emit an emission light at the first position on skin. According to various embodiments, the emitter may include a light emitting device, such as a light emitting diode or a light emitting laser diode. The emitter may include an optical guide, for example an optical fiber. The optical fiber may be optically coupled to the light emitting device. The emitter may be configured to emit light with a peak wavelength selected from 600 nm to 1000 nm, for example selected from 800 nm to 1000 nm, for example selected from 800 nm to 900 nm. Accordingly, the light emitting device may be configured to emit light with a peak wavelength selected from 600 nm to 1000 nm, for example selected from 800 nm to 1000 nm, for example selected from 800 nm to 900 nm. The light emitting device may be, for example, a laser diode, for example a vertical-cavity surface-emitting laser (VCSEL). In one example the light emitting device may be a VCSEL 850 nm laser diode. In another example, the emitter may be a VCSEL 850 nm laser diode coupled to an optical guide. It was found that with a laser diode a good signal to noise ratio may be obtained for the vibration signal. It was also found that the vibration signal is more intense in the wavelength range between 800 nm to 1000 nm, including the wavelength range from 800 nm to 900 nm.

According to various embodiments, the receiver may be configured to, receive a diffused light from the emission light at the second position on skin. According to various embodiments, the receiver may include a light detector, for example a photodetector, such as a photodiode or a phototransistor. The photodetector may include biasing and/or amplifying circuitry. The receiver may include an optical guide, for example an optical fiber. The optical fiber may be optically coupled to the light detector. The receiver may be configured to sense light at the peak wavelength of the emitter. In one example the receiver may be a broadband photodiode covering VIS-NIR (e.g. with wavelength range between 600 nm to 1000 nm). In another example, the receiver may be a broadband photodiode covering VIS-NIR (e.g. with wavelength range between 600 to 1000 nm) coupled to an optical guide. In yet another example, the receiver may be configured to be responsive to wavelength from 800 nm to 900 nm, and may have a much lower or no responsivity out of this range.

According to various embodiments, the emitter and the receiver may be configured so that, when the emitter and the receiver are positioned on skin, the emitter is arranged to emit the emission light at the first position on skin and the receiver is configured to receive a diffused light from the emission light at the second position on skin. The second position is at a distance apart from the first position.

According to various embodiments, the emitter and the receiver may be in close contact, for example in direct contact, with the skin. Accordingly, the emitter and the receiver may be configured to be in close contact, such as in direct contact, with the skin. The term "close" in "close contact" may refer to a separation between the emitter and the skin and/or the receiver and the skin of less than the distance between the first position and the second position, for example, less than 1/10 of the distance, or less than 1/20 of the distance. For example the separation may be between 2 and 5 mm, in another example the separation may be equal to or less than 5 mm, in yet another example the separation may be less than 2 mm.

According to various embodiments, the emission light may include a wavelength which is able to at least partially diffuse through skin. The emission light wavelength may be adjusted to be able to measure the diffusion path length in the skin. The wavelength may be in the range of wavelengths from 600 nm to 1000 nm, for example from 800 nm to 1000 nm, for example from 800 nm to 900 nm. In accordance to various embodiments, a range described as from a first endpoint to a second endpoint, may include the first endpoint and the second endpoint.

According to various embodiments, the emitter and the receiver are configured to be positioned relative to each other, or are positioned relative to each other, to face substantially a same direction. The term "face" in this context means the side of the receiver and the emitter which is optically active. For example, the emitter is able to emit light in an emitter preferential direction, and the receiver is able to receive light from a receiver preferential direction, the emitter preferential direction and the receiver preferential direction are substantially parallel. For example the emitter and the receiver may be arranged substantially in a same plane, and facing away from a same side of the plane.

According to various embodiments, at least one of the first position and the second position is in proximity to a respiratory tract, for example in proximity to a trachea, along the neck area or around the chest area. It was found that the vibration signal has a stronger intensity in these areas.

According to various embodiments, the system may include a sensor module, wherein the sensor module includes the emitter and the receiver. The sensor module may include a casing. The emitter and the receiver may be arranged in fixed positions in relation to a casing of the sensor module.

According to various embodiments, the sensor module may be a necklace pendant. Alternatively or in addition, the sensor module may be a necklace. A necklace may be, for example, a band, a chain, or a cord that may be wrapped around the neck. A necklace pendant may be, for example, a pendant which may be attached, for example, so as to hang from, a necklace.

According to various embodiments, the sensor module may include a communication interface configured to transmit a vibration signal to a remote device.

According to various embodiments, the time may be equal to or longer than at least one breath cycle, for example the time may be at least 10 seconds, or in a further example, at least 5 seconds.

According to various embodiments, the system may include a circuit. The circuit may be configured to store a vibration signal corresponding to the light intensity of the diffused light received over a time. According to various embodiments, the system may include a processing unit. The processing unit may be configured to extract a respiratory parameter from the vibration signal.

According to various embodiments, the system may further include a remote device. The sensor module may be configured to transmit a vibration signal to the remote device. The remote device may be configured to receive a vibration signal from the sensor module. In some embodiments, the processing unit may be provided in the remote device. Also the processing unit may be provided in the remote device. For example, the remote device may be a computation device such as: a computer, a mobile phone, an electronic tablet.

According to various embodiments, the circuit and the processing unit may be integral parts of a same microprocessor. For example, the circuit and the processing unit may be implemented as sub-circuits of a microprocessor and/or programmed parts stored at least temporarily in a memory which may be included in the microprocessor.

The present disclosure relates to an optical approach towards direct-measurement of respiration, e.g. human respiration, via direct-contact. Respiration is an information-dense data stream: it has many components to it such as rate, depth, inhalation-to-exhalation ratio (IER), durations of inhalation, retention, exhalation, and hold, consistency, smoothness, transition, and so on. FIG. 1 shows a flowchart of the method 100 according to various embodiments. A first step 110 may include emitting an emission light at a first position on the skin and receiving a diffused light from the emission light at a second position on the skin. A second step 120 may include storing a vibration signal corresponding to a light intensity of the diffused light received over time. A third step 130 may include extracting a respiratory parameter from the vibration signal.

The principle behind the approach is optical diffuse reflectance. In this method, light is emitted from the emitter and is termed emission light or also incident light ($I_0$)). The emission light hits the skin surface tissue at the first position and diffuses on the skin subsurface, on a path (see FIG. 2, path 240) with a path length L, towards the receiver at the second position, which receiver collects the diffused light ($I_r$). The diffused light may also be named reflected light. The relationship between the diffused and emission light is expressed by Beer-Lambert Law:

$$I_r = I_0 e^{-\alpha L}.$$

The important part of this relationship is the Net Path Coefficient or αL (alpha×L), in which, α (alpha) is the path loss coefficient (in units of 1/cm) and L is the path length (cm). Due to tissue vibration when breathing, also named herein as the respiratory vibration, the Net Path Coefficient changes, causing the diffused light ($I_r$) to change and oscillate in time. It is this change in diffused light intensity that is picked up by detection elements to result in the breathing signal.

Figure 2:
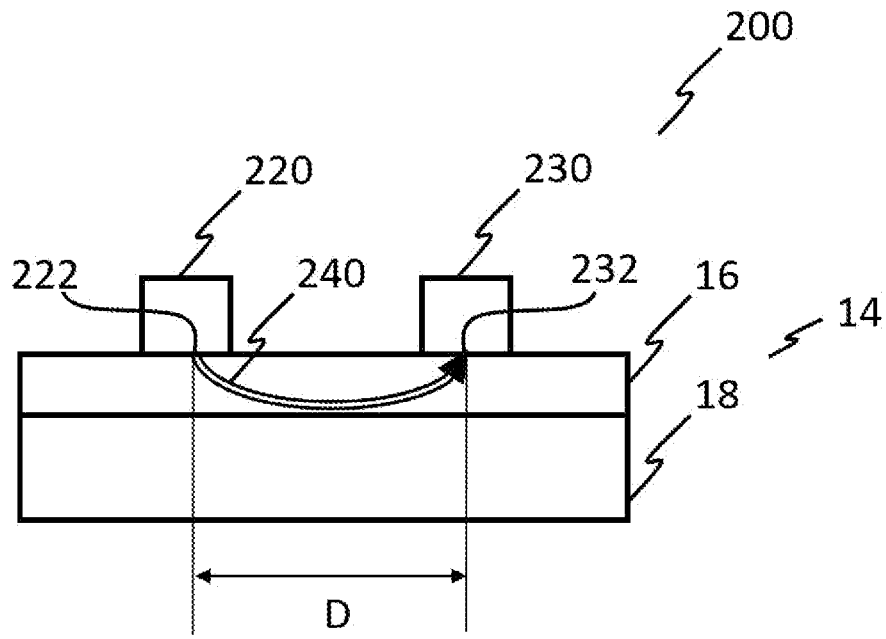
FIG. 2 is a schematic illustration of a system 200 according to various embodiments, and skin cross section 14 on which an emitter 220 and a receiver 230 are positioned for measuring respiratory vibration.

FIG. 2 is a schematic illustration of a system 200 and skin cross section 14 on which an emitter 220 and a receiver 230 are positioned for measuring respiratory vibration. The emitter 220 may be configured to emit an emission light at the first position 222 on skin. The receiver 230 may be configured to receive a diffused light from the emission light at the second position on skin 232. The second position 232 is at a distance D apart from the first position 222. The light diffusion path is schematically illustrated by the path 240. The length of the path 240 may be approximated to the distance D. The length of the path traversed by light along the skin may be for example 10 mm, within a depth of, for example, up to 5 mm. According to various embodiments the system is configured so that light is received from the dermis layer 16. Below the dermis layer is the subcutaneous fat layer 18, where blood concentration is typically higher. According to various embodiments, the vibration signal may be the signal obtained from the mechanical vibrations of the dermis layer 16 and may further exclude the signal from the underneath layers, such as layer 18, to avoid increase in signal noise. The system, the emitter, and/or the receiver may be configured accordingly, for obtaining the vibration signal from the dermis. Without wanting to be bound by theory, it is believed that the vibration signal from light modulated by the dermis may be of increased signal to noise ratio as from other skin layers.

Figure 3:
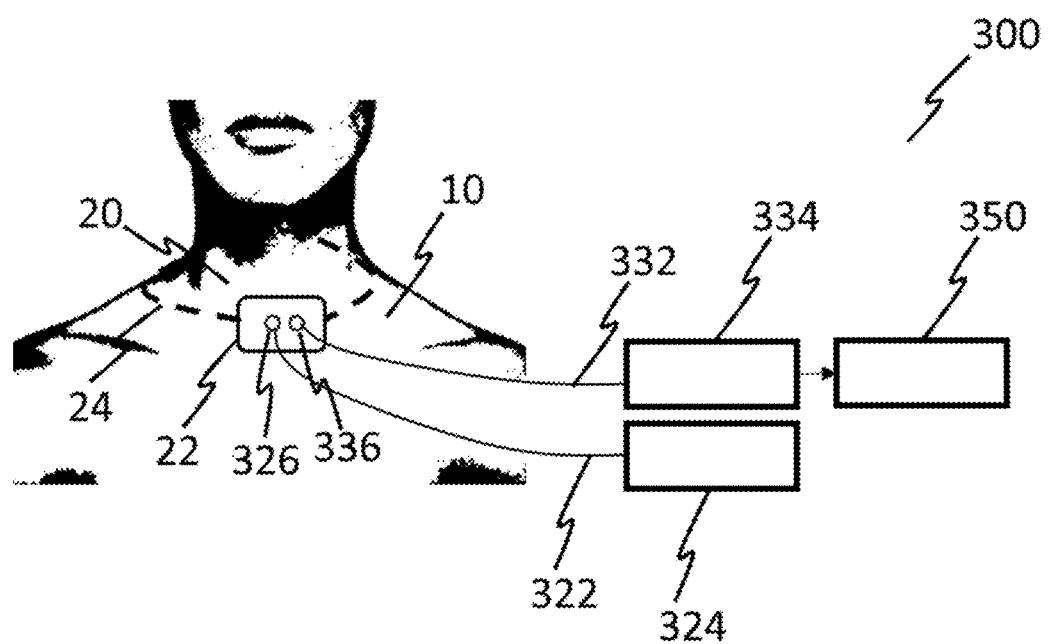
FIG. 3 is a schematic illustration of a system 300, wherein the optical fibers 322 and 332 touch the skin 10 around a neck area 20, in accordance to some embodiments.
Figure 4A:
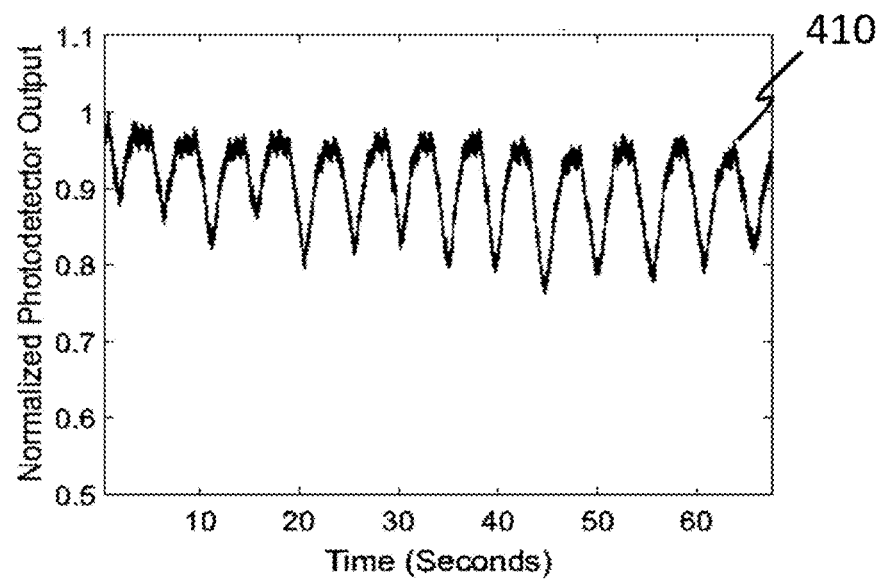
FIG. 4A shows a plot of vibration signal 410 in the form of receiver output over time acquired with a system 300 as illustrated in FIG. 3.
Figure 4B:
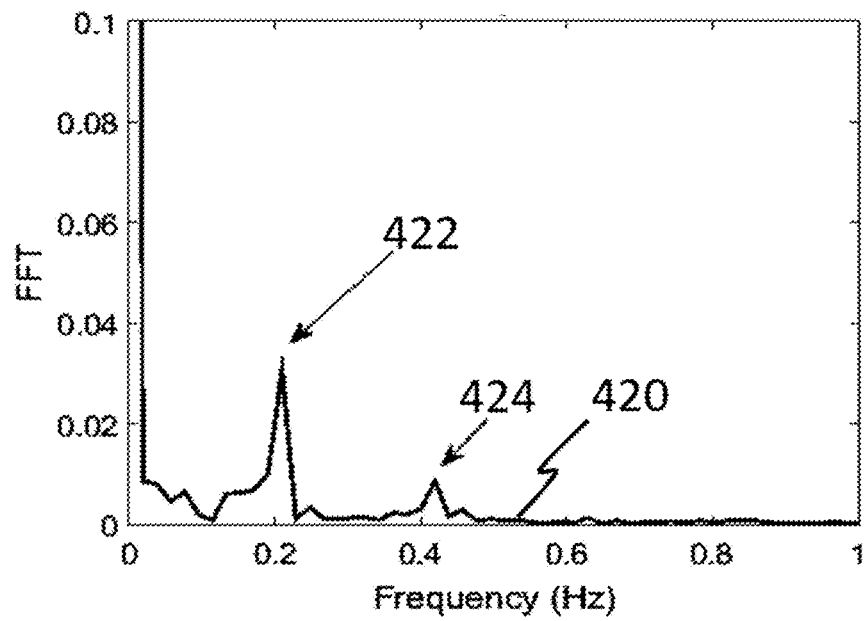
FIG. 4B shows an spectrum 420 of a Fast Fourier Transformation (FFT) of the signal 410.

FIG. 3 is a schematic illustration of a system 300 positioned on skin 10 around a neck area 20, in accordance to some embodiments. The system may be implemented in the form of an optical fiber coupled apparatus, the system comprising optical fibers (322 and 332) which optical fibers touch the skin, for example at positions 326 and 336 as illustrated in FIG. 3. In the example of FIG. 3, the emitter includes a light emitter 324 and an optical fiber 322 as optical guide, and the receiver includes a light receiver 334 and an optical fiber 332 as optical guide. In another example of FIG. 3, the optical fiber 322 of the light emitter 324 and the optical fiber 332 of the light receiver 334 may be positioned on a necklace pendant 22. Alternatively or in addition, the optical fiber 322 of the light emitter 324 and the optical fiber 332 of the light receiver 334 may be a necklace 24, for example, part of the necklace 24. As a further example, the necklace pendant 22 may be attached to the necklace 24, and may be placed on the neck area 20 of the skin 10. In a more concrete example in accordance to FIG. 3, an optical fiber 322 was placed on the neck area 20 at a first position 326. An optical fiber 332 was placed on the neck area 20 at a second position 336. The optical fiber 322 was coupled to a light-emitting diode 324 with peak emission wavelength at 850 nm. The optical fiber 332 was coupled to a silicon avalanche photodiode 334. The electrical signal produced by light interaction on the photodiode was post-processed by passing the electrical signal through a low-pass filter and computing the fast-Fourier transform (FFT). An example of electrical signal is the photocurrent of the photodiode, another example is a corresponding voltage, e.g. generated due to the flow of the photocurrent through a resistor. A conversion from analog to digital signal may be included as necessary, for example before the FFT, or before the low-pass filter if the low-pass filter is a digital filter. FIGS. 4A and 4B present the post processed results obtained with a system as shown in FIG. 3. FIG. 4A shows a plot of a vibration signal 410 in the form of receiver output over time acquired with a system 300, namely the time-domain vibration signal, which in this example includes a clear breathing signal under normal respiratory condition. In the breathing signal, the periodic intensity modulation at the rate of respiration is seen. The FFT 420 of the vibration signal 410 is shown in FIG. 4B, where the fundamental respiratory rate at 0.21 Hz (peak 422) and the second harmonic at 0.4 Hz (peak 424) is seen. This corresponds rightly to the breathing period of around 4.76 seconds and approximately 12.6 breaths per minute. According to various embodiments, the second or higher harmonics, e.g. peak 424 as illustrate in FIG. 4B, may be filtered out using the low pass filter.

Figure 5:
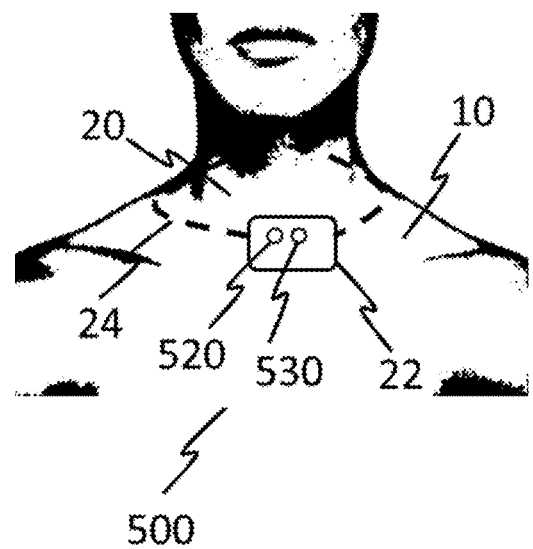
FIG. 5 is a schematic illustration of a system 500, positioned on skin 10 around a neck area 20, in accordance to some embodiments, wherein the light emitter and light receiver may be in close contact with the skin and thus no optical fibers are required.

FIG. 5 is a schematic illustration of a system 500 positioned on skin 10 around a neck area 20, in accordance to some embodiments. In the example of FIG. 5, the emitter 520 includes a light emitter and the receiver 530 includes a light receiver. The system 500 may be implemented as a direct contact apparatus, for example, wherein the light emitter and light receiver may each be configured to be in close contact with the skin, and may each be in close contact with the skin. In an example of FIG. 5, the emitter 520 and the receiver 530 may be positioned on a necklace pendant 22. Alternatively or in addition, the emitter 520 and the receiver 530 may be a necklace 24, for example part of a necklace 24. The necklace pendant 22 may be connected to a necklace 24, and placed on the neck area 20 of the skin 10.

Figure 6A:
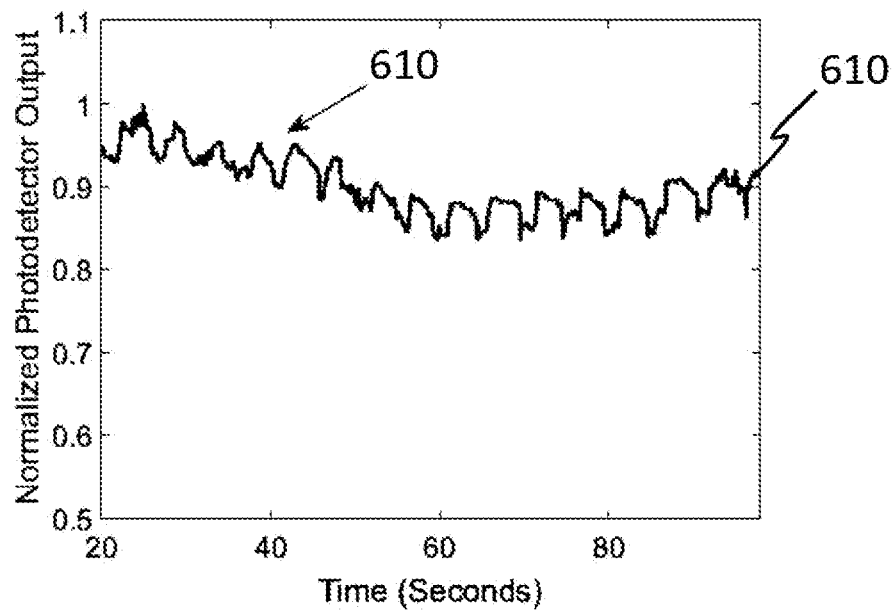
FIG. 6A shows a plot of vibration signal 610 in the form of receiver output over time acquired with a system 500 of FIG. 5, according to various embodiments.
Figure 6B:
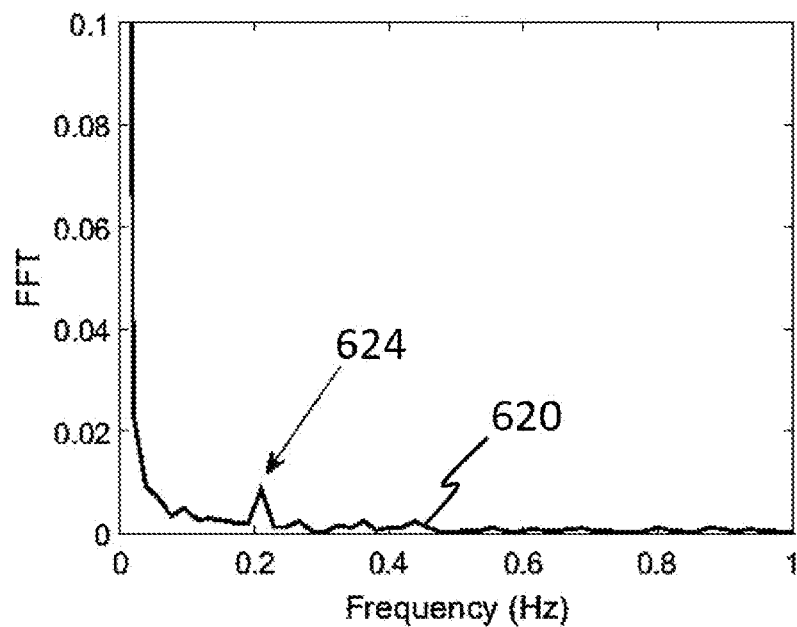
FIG. 6B shows an spectrum 620 of a Fast Fourier Transformation (FFT) of the signal 610.

FIG. 6A shows a plot of a vibration signal 610 in the form of receiver output over time acquired with a system 500 of FIG. 5, namely the time-domain vibration signal, in this case including a clear breathing signal, under normal respiratory condition. The FFT 620 of the vibration signal 610 is shown in FIG. 6B, where the fundamental respiratory rate can be seen at the peak 624 at 0.21 Hz. The results of FIGS. 6A and 6B were taken with a VCSEL 850 nm laser diode as emitter and a broadband photodiode detector covering VIS-NIR (600-1000 nm) as receiver. The distance between 850 nm diode and the receiver was 10 mm.

Figure 7A:
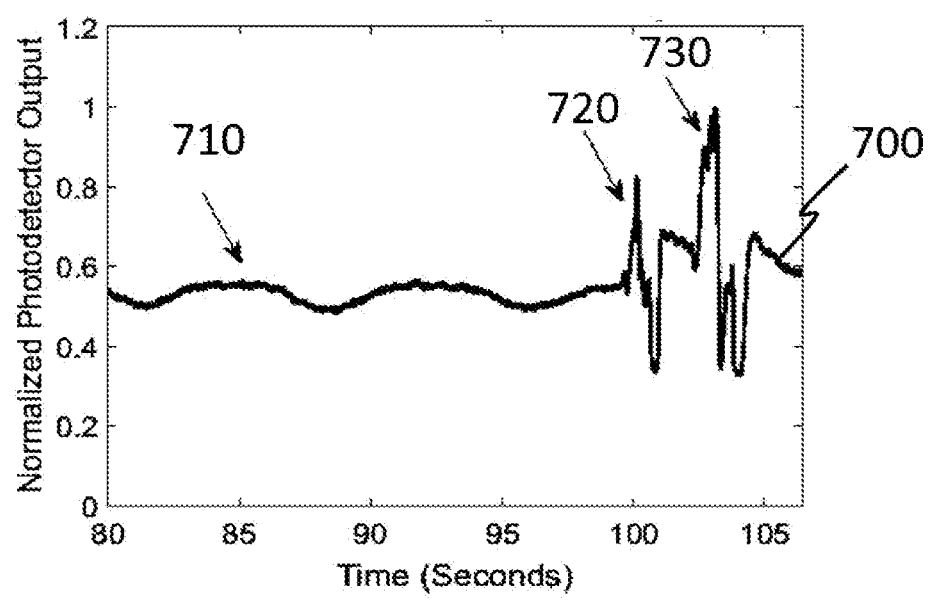
FIG. 7A shows a plot of vibration signal 700 representing breathing in the region 710 and to cough events 720 and 730.
Figure 7B:
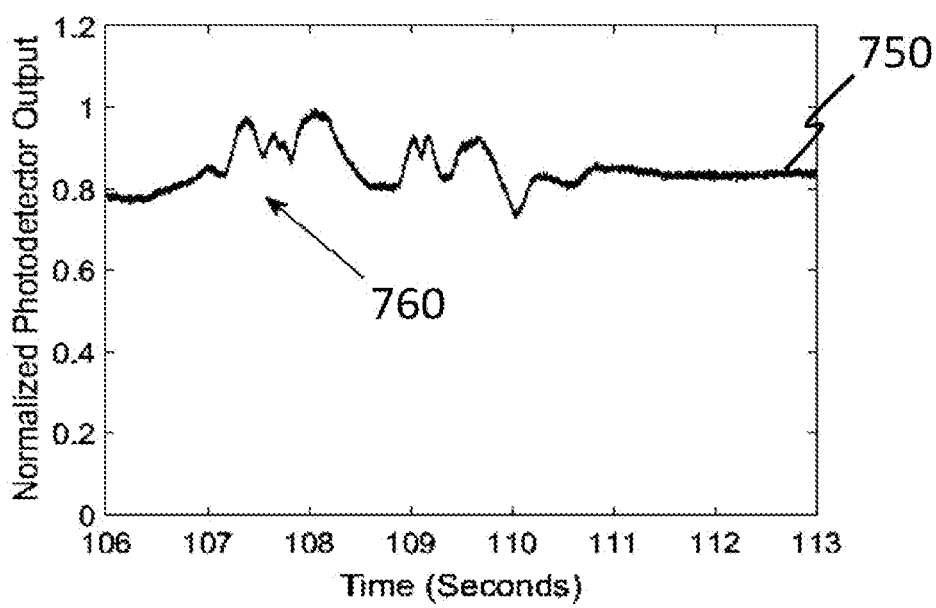
FIG. 7B shows a plot of vibration signal 750 representing breathing modulated by speech in region 760.

In FIG. 7A, an example of a vibration signal 700 is presented under the condition of normal breathing, in region 710, followed by 2 coughs and 3 coughs. This post-processed signal was taken with a system according to FIG. 5, but similar results can be obtained with any other system according to various embodiments, for example with a system according to FIG. 3. Two distinct spikes are observed upon 2 coughs in region 720 while three distinct spikes are observed upon 3 coughs in region 730. FIG. 7B shows a plot of vibration signal 750 representing breathing modulated by speech of "Hello World" and "Good morning".

According to various embodiments, the system may be implemented as a device, for example a wearable device. The device can quickly, easily and accurately measure breathing rate and patterns around the human neck area. The applications of this device include clinical respiratory monitoring and general consumer healthcare, for example, in measuring stress levels from respiration patterns. Further embodiments and examples of systems and devices will be shown in connection with FIGS. 8A-8C.

In the examples illustrated in FIGS. 8A, 8B, 8C, 9A, 9B, 10, 11 and 12, systems implemented as apparatuses were used, for example wherein all electronic and optic components may be integrated as a wearable apparatus.

Figure 8A:
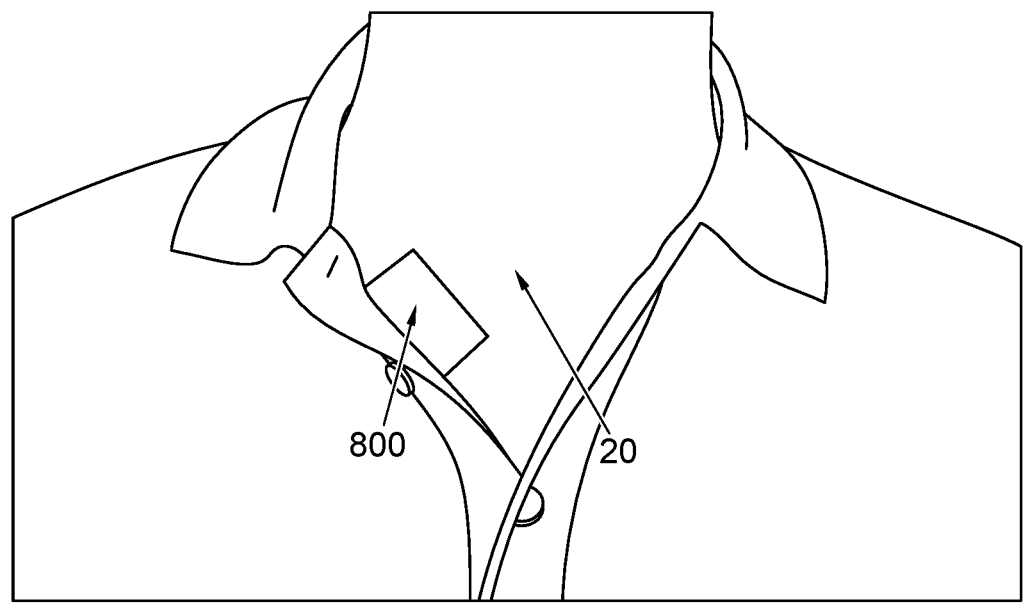
FIG. 8A shows an assembled set of a sensor module 860 and a skin adhesive patch 870, according to various embodiments, applied to a person's neck 20.
Figure 8B:
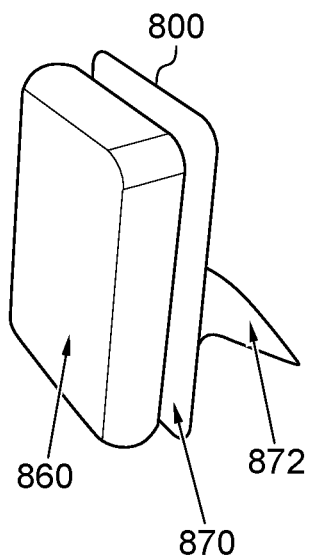
FIG. 8B shows a closer view of the assembled set of the sensor module 860 and the skin adhesive patch 870 of FIG. 8A, with an adhesive protection layer 872 partially removed.
Figure 8C:
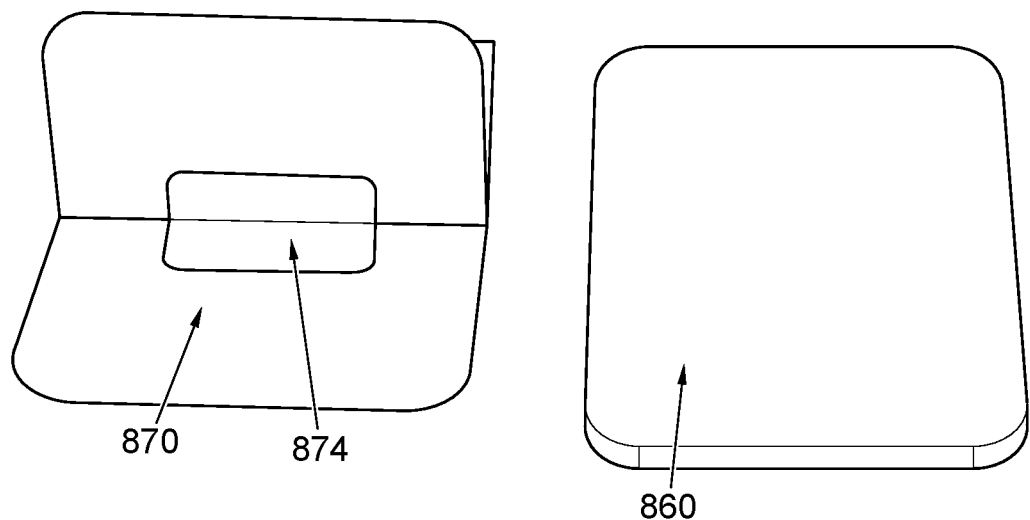
FIG. 8C shows a closer view of the skin adhesive patch 870 of FIGS. 8A and 8B, and the sensor module 860, in unassembled state.

FIG. 8A shows an exemplary set of a sensor module 860 and a skin adhesive patch 870, according to various embodiments, in assembled form and applied to a person's neck 20. In some embodiments, the sensor module 860 may be a necklace pendant 22. Alternatively, or in addition, the sensor module 860 may be a necklace 24. For example, the necklace pendant 22 including the sensor module 860 may be attached to the necklace 24 and may hang from the necklace 24. A skin adhesive patch may be provided to connect the device onto the neck area of the subject. The sensor module 860 may be assembled to the skin adhesive patch 870, by a suitable fastening means, for example, by a hook and loop fastener. In one example, one side of the skin adhesive patch is a sticky part that sticks to the subject neck area, and the other side of the skin adhesive patch may include hook and loop fastener that sticks to the sensor module. FIG. 8B shows a closer view of the assembled set of the sensor module 860 and the skin adhesive patch 870 of FIG. 8A, still with an adhesive protection layer 872 partially removed. FIG. 8C shows a closer view of the skin adhesive patch 870 of FIGS. 8A and 8B, and the sensor module 860, in unassembled state. The skin adhesive patch 870 may include a window region window 874, configured to allow optical coupling of the emitter to skin, and of the receiver to skin. The window region may be, for example a transparent window or a cut out, which allows the emission light from the sensor module to make contact with the subject and the diffused light to be detected. The skin adhesive patch may be disposable so that it can be disposed after usage.

FIG. 8A highlights how the system may be worn around the neck area, according to some embodiments. In other embodiments, the sensor module may be worn as a necklace pendant.

Figure 9A:
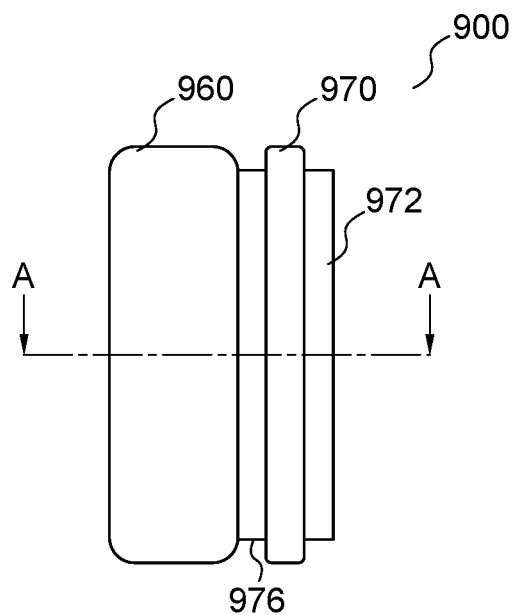
FIG. 9A is a schematic illustration of an assembled set 900 of a sensor module 960 and a skin adhesive patch 970.

FIG. 9A is a schematic illustration of an assembled set 900 of a sensor module 960 and a skin adhesive patch 970. The skin adhesive patch 970 may include an adhesive layer 972 configured for adhering the skin adhesive patch 970 to skin. The set may include a fastening means 976 for removable fastening the sensor module 960 to the skin adhesive patch 970. The fastening means 976 may be, for example a single layer, or more than one layer, for example it may be a hook and loop fastener.

Figure 9B:
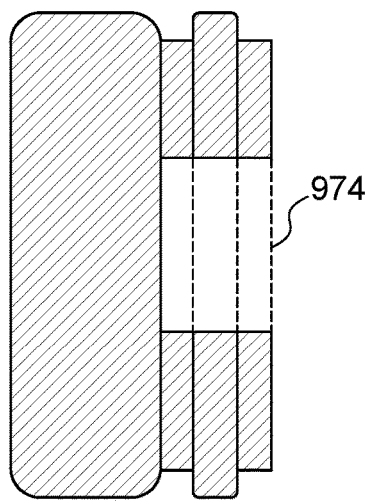
FIG. 9B is a cross-sectional view A-A of the assembled set 900 for illustrating an example of a window region 974.

FIG. 9B is a cross-sectional view A-A of the assembled set 900 for illustrating an example of a window region 974. In the illustrated example, the skin adhesive patch 970 includes a window for providing the window region 974, the window may be a cutout or a transparent region. The window region 974 may also be free of adhesive layer 972 and may be free of fastening means 976.

While FIG. 8A-9B describe various embodiments in connection with a set of a sensor module 860 and a skin adhesive patch 870, it is emphasized that the explanations and description of the features also apply to a system and vice-versa, and also to a method and vice-versa, in accordance to various embodiments.

The gold-standard of measuring respiration in the clinics or hospitals is by manual-counting. A study was conducted and the table below compares the breathing rate measured by a system in accordance to various embodiments and the gold-standard of manual-counting. The study consisted of healthy subjects from a broad age group. As can be seen, deviations of less than 1 bpm (bpm means breaths per minute) can be achieved.

| Subjects (Age, Gender, Weight, Skin Tone) | Manual (bpm) | Device (bpm) |
| --- | --- | --- |
| A (34, M, Normal, Dark) | 9 | 8.5 |
| B (27, M, Normal, Fair) | 7 | 6.5 |
| C (64, F, Overweight, Fair) | 10 | 10.5 |
| D (59, M, Normal, Fair) | 10 | 10.2 |
| E (31, M, Normal, Fair) | 14 | 13.4 |

Figure 10:
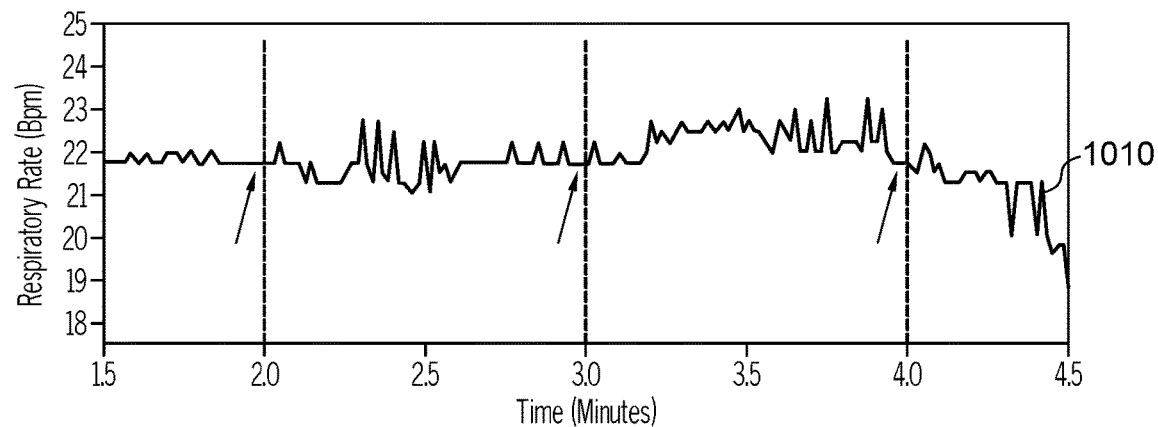
FIG. 10 shows an upper plot 1010, of a vibration signal wherein the respiratory rate can be seen over a continuous period of 3 minutes, and a lower plot 1020.
Figure 10:
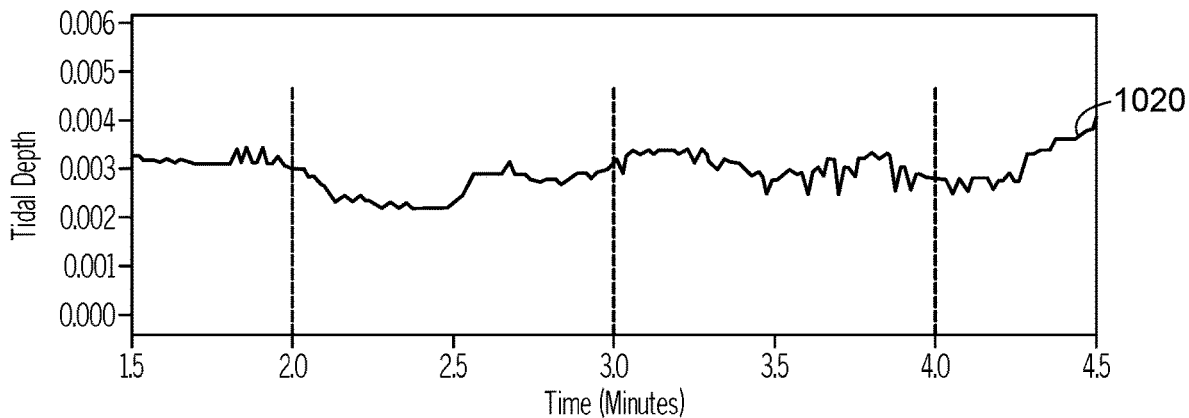

A proof-of-concept was also done on patients in the intensive-care-unit. One example of a comparison of the results of the gold standard (manual counting) and the method and system according to various embodiments is shown in FIG. 10. It is shown an upper plot 1010 of a vibration signal wherein the respiratory rate can be seen over a continuous period of 3 minutes, and a lower plot 1020. Plot 1020 shows the tidal depth or the depth of breathing. This is measured as the displacement between the maximum to minimum of the electrical signal. As can be seen, the tidal depth and breathing pattern are both consistent over the breathing. FIG. 10 shows an exemplary plot of the respiratory rate over a continuous period of 3 mins and compares with manual-counting at intervals of 1 min. The manual count is 21 counts at the mark of 2 minutes, another 22 counts at mark of 3 minutes, and another 21 counts at the mark of 4 minutes. For this study the highly-severe disease patients, the average deviation from manual-count and ECG-leads were 1.54 bpm and 1.21 bpm, respectively.

Figure 11:
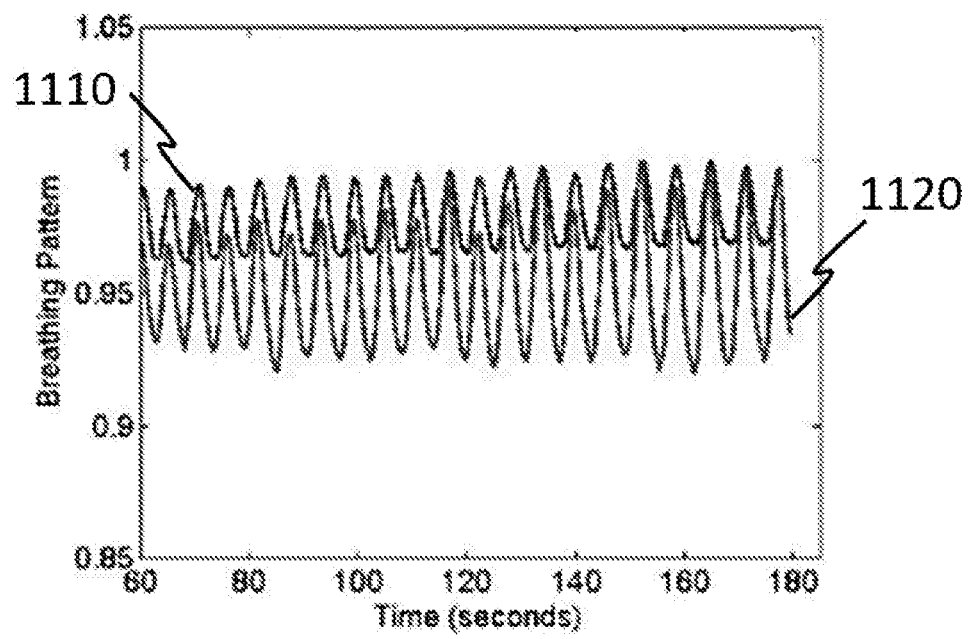
FIG. 11 shows a comparison of a respiratory rate signal acquired, in accordance to various embodiments, in a lower plot 1120 to a respiratory rate signal acquired with a commercial product, using a different technique, in an upper plot 1110.

FIG. 11 shows a comparison of a respiratory rate signal acquired in accordance to various embodiments in a lower plot 1120 to a respiratory rate signal acquired with a commercial product, using a different technique (Zephyr Bioharness from the company Medtronic), in an upper plot 1110. As can be seen from FIG. 11, which plots the breathing pattern over time, a good match can be achieved with the commercial product.

The results of FIGS. 10 and 11 were taken with a VCSEL 850 nm laser diode as emitter and a broadband photodiode detector covering VIS-NIR (600-1000 nm) as receiver. The distance between 850 nm diode and the receiver was 10 mm.

The sensor module may include a single chip performing various task, for example at least one, of: power supply, switching module, calibration module, optical sensing, signal processing, signal transmission, wireless Bluetooth transmission, or combinations thereof.

Figure 12:
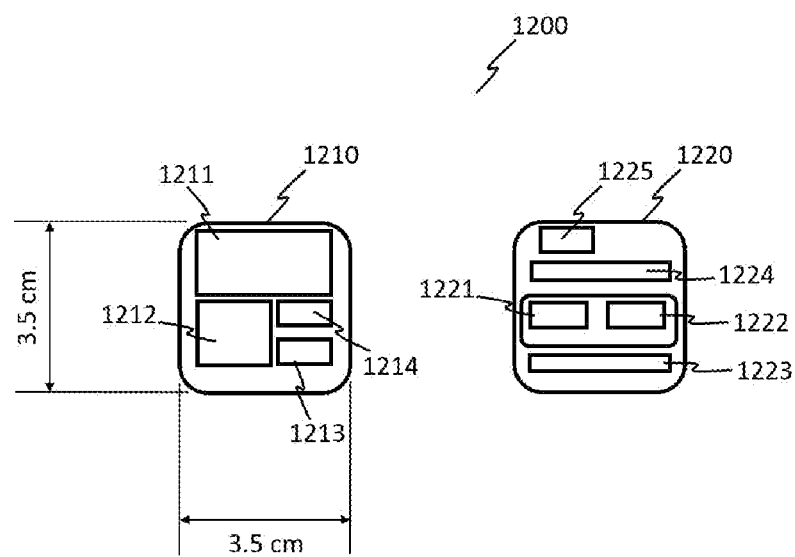
FIG. 12 shows an example of a schematic layout of the electronic components of a sensor module 1200 according to various embodiments.

In one example, the sensor module includes several components as shown in FIG. 12. The sensor module 1200 may include, for example on a first side 1210, at least one of a battery 1211, such as a 180 mAh battery, a wireless transmitter 1212, such as a Bluetooth transmitter, a charging circuit, such as an USB charging connector and/or circuit 1214, a voltage tuner 1213 to tune the power of the emitter. The sensor module 1200 may include, for example on a second side 1220, at least one of an emitter 1221, such as an LED or a laser diode, a receiver 1222, such as an integrated photodiode, a microprocessor 1223, such as a programmable microprocessor, a memory 1224, such as a 32 MB memory, a switch 1225, for example to turn the device on and off. The microprocessor may be configured to perform the required analog to digital conversion and signal processing. The memory may be configured, for example, to store relevant boot-up software data and past history. The wireless transmitter, e.g. the Bluetooth transmitter, may be configured to receive and transmit data wirelessly to mobile platforms such as a computer and a mobile phone.

While the invention has been particularly shown and described with reference to specific embodiments, it should be understood by those skilled in the art that various changes in form and detail may be made therein without departing from the scope of the invention as defined by the appended claims. The scope of the invention is thus indicated by the appended claims and all changes which come within the meaning and range of equivalency of the claims are therefore intended to be embraced.

The invention claimed is:

1. A method for measuring respiratory vibration on a human or animal skin, comprising:
  emitting an emission light at a first position on the skin;
  receiving a diffused light from the emission light at a second position on the skin, wherein the second position is at a distance apart from the first position;
  storing a vibration signal comprising a light intensity of the diffused light received over time; wherein the vibration signal corresponds to a mechanical vibration from a dermis layer of the skin, wherein the mechanical vibration is due to an expansion and contraction of a membrane below the skin; and
  extracting a respiratory parameter from the vibration signal.

2. The method of claim 1, further comprising applying a low-pass filter on the vibration signal.

3. The method of claim 1, further comprising generating a spectrum in the frequency domain from the vibration signal, which is in the time domain.

4. The method of claim 1, wherein extracting the respiratory parameter comprises determining at least one of: breath cycle count, frequency, rate, depth, inhalation-to-exhalation ratio (IER), durations of inhalation, retention, exhalation, hold, consistency, smoothness, transition.

5. The method of claim 1, wherein extracting the respiratory parameter comprises determining one or more cough events.

6. The method of claim 1, wherein extracting the respiratory parameter comprises determining one or more speech events.

7. The method of claim 1, wherein at least one of the first position and the second position is in proximity to or at a trachea, a neck or a chest.

8. A system for measuring respiratory vibration on a human or animal skin, comprising:
- an emitter configured to emit an emission light at a first position on the skin;
- a receiver configured to receive a diffused light from the emission light at a second position on the skin,
- wherein the second position is at a distance apart from the first position;
- a circuit configured to store a vibration signal corresponding to a light intensity of the diffused light received over time, wherein the vibration signal corresponds to a mechanical vibration from a dermis layer of the skin, wherein the mechanical vibration is due to an expansion and contraction of a membrane below the skin; and
- a processing unit configured to extract a respiratory parameter from the vibration signal.

9. The system of claim 8, wherein the time is equal to or longer than at least one breath cycle.

10. The system of claim 8, wherein the system comprises a sensor module, wherein the sensor module comprises the emitter and the receiver.

11. The system of claim 10, wherein the sensor module is a necklace pendant or a necklace.

12. The system of claim 8, wherein the emitter and the receiver are positioned relative to each other to face substantially a same direction.

13. The system of claim 10, wherein the sensor module comprises the circuit.

14. The system of claim 8, further comprising a remote device and wherein at least one of the circuit and the processing unit is provided in the remote device.

15. The system of claim 8, wherein the circuit and the processing unit are integral parts of a same microprocessor circuit.

16. The system of claim 8, wherein at least one of the first position and the second position is in proximity to or at a trachea, a neck or a chest.

17. The system of claim 8, wherein the emitter comprises a light emitting diode or a light emitting laser diode, and wherein the receiver comprises a photodetector.

18. The system of claim 8, wherein at least one of the emitter and the receiver comprises a respective optical guide.

19. The system of claim 8, wherein the emission light comprises a wavelength which is able to at least partially diffuse through skin.

20. A set of a sensor module and a skin adhesive patch, wherein the skin adhesive patch comprises a first surface which may be placed on a skin and a second surface which may cooperate with the sensor module to fixate the sensor module to the patch; wherein the sensor module comprises:
- an emitter configured to emit an emission light at a first position on the skin;
- a receiver configured to receive a diffused light from the emission light at a second position on the skin;
- wherein the second position is at a distance apart from the first position;
- a circuit configured to store a vibration signal corresponding to a light intensity of the diffused light received over a time,
- wherein the vibration signal corresponds to a mechanical vibration from a dermis layer of the skin, and
- wherein the mechanical vibration is due to an expansion and contraction of a membrane below the skin;
- wherein the patch comprises a window region, configured to allow optical coupling of the emitter to the skin, and of the receiver to the skin.

* * * * *